US011000781B2

(12) United States Patent
Martin et al.

(10) Patent No.: US 11,000,781 B2
(45) Date of Patent: May 11, 2021

(54) PURIFYING AQUEOUS SOLUTIONS

(71) Applicant: DDP SPECIALTY ELECTRONIC MATERIALS US 8, LLC, Collegeville, PA (US)

(72) Inventors: Collin H. Martin, North Wales, PA (US); Stephen Pease, Ambler, PA (US)

(73) Assignee: DDP SPECIALTY ELECTRONIC MATERIALS US 8, LLC, Collegeville, PA (US)

( * ) Notice: Subject to any disclaimer, the term of this patent is extended or adjusted under 35 U.S.C. 154(b) by 198 days.

(21) Appl. No.: 15/769,369

(22) PCT Filed: Nov. 1, 2016

(86) PCT No.: PCT/US2016/059888
§ 371 (c)(1),
(2) Date: Apr. 19, 2018

(87) PCT Pub. No.: WO2017/079145
PCT Pub. Date: May 11, 2017

(65) Prior Publication Data
US 2018/0304172 A1 Oct. 25, 2018

Related U.S. Application Data

(60) Provisional application No. 62/250,698, filed on Nov. 4, 2015.

(51) Int. Cl.
| | |
|---|---|
| *B01D 15/36* | (2006.01) |
| *C13K 13/00* | (2006.01) |
| *B01J 39/20* | (2006.01) |
| *C13K 3/00* | (2006.01) |
| *B01J 47/014* | (2017.01) |
| *B01D 15/18* | (2006.01) |
| *C07D 307/48* | (2006.01) |
| *C08L 41/00* | (2006.01) |

(52) U.S. Cl.
CPC ............ *B01D 15/362* (2013.01); *B01J 39/20* (2013.01); *B01J 47/014* (2017.01); *C13K 3/00* (2013.01); *C13K 13/007* (2013.01); *B01D 15/1821* (2013.01); *B01D 2257/70* (2013.01); *C07D 307/48* (2013.01); *C08L 41/00* (2013.01)

(58) Field of Classification Search
None
See application file for complete search history.

(56) References Cited

U.S. PATENT DOCUMENTS

| | | | |
|---|---|---|---|
| 3,066,150 A | 11/1962 | Jones et al. | |
| 4,160,675 A | 7/1979 | Pannekeet et al. | |
| 5,081,160 A * | 1/1992 | Strom | B01J 39/20 521/29 |
| 9,068,206 B1 * | 6/2015 | Kwiatkowski | C12P 17/10 |
| 2003/0006191 A1 * | 1/2003 | Heikkila | B01D 15/1828 210/656 |
| 2009/0018352 A1 | 1/2009 | Geier et al. | |
| 2009/0176897 A1 * | 7/2009 | Finch | C08F 2/12 521/38 |
| 2016/0194727 A1 | 7/2016 | Pease et al. | |
| 2018/0016649 A1 * | 1/2018 | Kavakka | C13K 13/002 |

FOREIGN PATENT DOCUMENTS

EP 0327400 A2 8/1989

OTHER PUBLICATIONS

De Mancilha et al, Evaluation of Ion Exchange Resins for Removal of Inhibitory Compounds from Corn Stover Hydrolyzate for Xylitol Fermentation, Biotechnol. Prog. 2003, vol. 19, pp. 1837-1841. (Year: 2003).*
Product Data Sheet for Purolite C155S Polystyrenic Macroporous Strong Acid Cation Exchange Resin in Sodium Form. (Year: 2020).*
Agirrezabal-Telleria, et al., "Furfural production from xylose using sulfonic ion-exchange resins (Amberlyst) and simultaneous stripping with nitrogen", Bioresource Technology, vol. 102, pp. 7478-7485 (2011).
Carter, et al., Removal and Recovery of Furfural, 5-Hydroxymethylfurfural, and Acetic Acid From Aqueous Solution Using a Soluble Polyelectrolyte, Biotechnology and Bioengineering, vol. 108, No. 9 pp. 2046-2052 (2011).
Carter, et al., "Detoxification of a Lignocellulosic Biomass Slurry by Soluble Polyelectrolyte Adsorption for Improved Fermentation Efficiency", Biotechnology and Bioengineering, vol. 108, No. 9 (2011).
Zhang, et al., "Removal of the Fermentation Inhibitor, Furfural, Using Activated Carbon in Cellulosic-Ethanol Production", Ind. Eng. Chem. Res., vol. 50, pp. 14055-14060 (2011).
Nilvebrant, et al., "Detoxification of Lignocellulose Hydrolysates with Ion-Exchange Resins", App. Biochemistry and Biotechnology, vol. 91-93, pp. 35-49 (2001).

* cited by examiner

*Primary Examiner* — Matthew O Savage
(74) *Attorney, Agent, or Firm* — Carl P. Hemenway; Kenneth Crimaldi

(57) ABSTRACT

Provided is a process for purifying an aqueous solution, wherein the aqueous solution comprises one or more sugars and additionally comprises furfural, hydroxymethylfurfural, or a mixture thereof; wherein the process comprises passing the aqueous solution through a collection of resin particles; and wherein the resin particles comprise covalently bound acid functional groups.

4 Claims, No Drawings

PURIFYING AQUEOUS SOLUTIONS

It is sometimes desirable to separate furfurals (i.e., furfural and hydroxymethyl furfural) from other compounds dissolved in aqueous solutions. For example, materials from vegetation may be processed, for example by chemicals, heat, and/or enzymatic action, to produce an aqueous solution that contains one or more sugars. Such processes often produce aqueous solutions that contain, in addition to one or more sugars, furfural or hydroxymethyl furfural or a mixture thereof. Such an aqueous solution often additionally includes one or more organic acid, one or more alcohol, one or more inorganic salt, or a combination thereof. It is often desired to use such an aqueous solution in a fermentation process to produce, for example, ethanol. However, the furfurals are known to inhibit fermentation processes. Therefore it is desired to remove the furfurals from the aqueous solutions.

N. Nilvebrant, et. al, in "Detoxification of Lignocellulose Hydrolysates with Ion-Exchange Resins," *Applied Biochemistry and Biology*, volume 91-93, pages 35-49, 2001, describe a batch process for detoxification of lignocellulose hydrolysates with ion-exchange resins. It is desired to provide a pass-through method for separating furfurals from sugars and other compounds. It is further desired that the pass-through method separate furfurals without binding the furfurals to a resin, because such binding would mean that the resin would need to be periodically taken out of service and subjected to a process of regeneration to remove the bound furfurals.

The following is a statement of the invention.

A first aspect of the present invention is a process for purifying an aqueous solution, wherein the aqueous solution comprises one or more sugars and additionally comprises furfural, hydroxymethylfurfural, or a mixture thereof; wherein the process comprises passing the aqueous solution through a collection of resin particles, wherein the resin particles comprise covalently bound acid functional groups.

The following is a detailed description of the invention.

As used herein, the following terms have the designated definitions, unless the context clearly indicates otherwise.

Organic compounds are compounds that contain carbon, excluding compounds generally considered to be inorganic. Carbon-containing compounds that are generally considered to be inorganic include the following: binary oxides and sulfides of carbon; ternary metallic cyanides, ternary metallic carbonyls, phosgene, carbonyl sulfide; and metallic carbonates.

"Resin" as used herein is a synonym for "polymer." A "polymer," as used herein is a relatively large molecule made up of the reaction products of smaller chemical repeat units. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof. Polymers have weight-average molecular weight of 2,000 or more.

Molecules that can react with each other to form the repeat units of a polymer are known herein as "monomers." The repeat units so formed are known herein as "polymerized units" of the monomer.

Vinyl monomers have the structure I

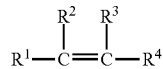

where each of $R^1$, $R^2$, $R^3$, and $R^4$ is, independently, a hydrogen, a halogen, an aliphatic group (such as, for example, an alkyl group), a substituted aliphatic group, an aryl group, a substituted aryl group, another substituted or unsubstituted organic group, or any combination thereof. Vinyl monomers have molecular weight of less than 1,000. Vinyl monomers include, for example, styrene, substituted styrenes, dienes, ethylene, ethylene derivatives, and mixtures thereof. Ethylene derivatives include, for example, unsubstituted and substituted versions of the following: vinyl acetate and acrylic monomers. Acrylic monomers are monomers selected from substituted and unsubstituted (meth)acrylonitrile, (meth)acrylic acid, substituted and unsubstituted alkyl esters of (meth)acrylic acid, substituted and unsubstituted amides of (meth)acrylic acid, and mixtures thereof. As used herein, the prefix "(meth)acryl-" means either acryl- or methacryl-. "Substituted" means having at least one attached chemical group such as, for example, alkyl group, alkenyl group, vinyl group, hydroxyl group, alkoxy group, carboxylic acid group, phosphoric acid group, sulfonic acid group, amino group, substituted amino group, other functional groups, and combinations thereof.

As used herein, vinyl aromatic monomers are vinyl monomers in which one or more of $R^1$, $R^2$, $R^3$, and $R^4$ contain one or more aromatic ring.

A monovinyl monomer is a vinyl monomer that has exactly one non-aromatic carbon-carbon double bond per molecule. A multivinyl monomer is a vinyl monomer that has two or more non-aromatic carbon-carbon double bonds per molecule.

A vinyl polymer is a polymer in which 90% or more of the polymerized units, by weight based on the weight of the polymer, are polymerized units of one or more vinyl monomers. An acrylic polymer is a vinyl polymer in which 50% or more of the polymerized units, by weight based on the weight of the polymer, are acrylic monomers.

A collection of particles is characterized by the diameters of the particles. If a particle is not spherical, the diameter of the particle is considered to be the diameter of a particle having the same volume as the particle. A collection of particles is characterized herein by the parameters D10, D50, and D60. D10 is the value such that exactly 10% of the collection of particles by volume have diameter of D10 or less. D50 is the value such that exactly 50% of the collection of particles by volume have diameter of D50 or less. D60 is the value such that exactly 60% of the collection of particles by volume have diameter of D60 or less. The parameters D10, D50, and D60 are determined by mixing a sample of the collection of particles into water to form a dilute slurry and using laser light scattering to determine D10, D50, and D60.

A collection of particles may also be characterized by the uniformity coefficient (UC), which is defined herein as UC=D60/D10.

The collection of resin particles occupies a total volume of space that includes the resin particles and also includes the interstitial volumes that are present in between adjacent resin particles. This total volume is known herein as the bed volume (BV). The bed volume is larger than the total volume of the resin particles, which only includes the volumes of the resin particles themselves and not the interstitial volumes.

Some resin particles are macroporous, which means that the particles have pores with an average pore diameter of 50 nm or larger. Pore diameter is determined by the Brunauer-Emmett-Teller (BET) method. Resin particles that have no pores or that have pores of average diameter less than 50 nm are gel resin particles.

Acid-functional resins are characterized by the total capacity of the resin. Total capacity is measured by preparing a known volume of settled resin in hydrogen form, wet with water. The resin is wet-packed with water into a chromatography column, and a molar excess of sodium sulfate in aqueous solution is passed through the column and collected, followed by water. All the aqueous sodium sulfate and water that passed through the column is collected into a vessel, and the resulting sample solution is titrated with a standardized sodium hydroxide solution. The equivalents of sodium hydroxide required to neutralize the sample solution is divided by the original volume of the resin to determine the resin capacity in equivalents per Liter of resin (eq/L).

As used herein, the term sugar refers to a monosaccharide, a mixture of monosaccharides, a disaccharide, a mixture of disaccharides, or a mixture of one or more monosaccharides with one or more disaccharides.

As used herein, organic acids are organic compounds capable of releasing a hydrogen atom and having pKa of 6 or less. Compounds having more than one pKa are characterized herein by the lowest pKa. As used herein, alcohols are compounds having the structure $R^5$—OH, where $R^5$ is a substituted or unsubstituted hydrocarbyl group. As used herein, inorganic salts are compounds having the structure MA, where M is either an ammonium cation or a cation of a metal atom (including transition metals), a cation of an alkaline earth atom, or a cation of an alkali metal atom; and A is an anionic group, which may be a single atom or a group of atoms.

Furfural has the structure

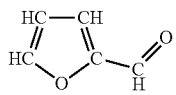

and hydroxymethylfurfural has the structure

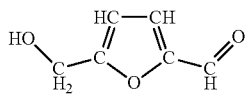

The present invention involves the use of a collection of resin particles. Preferably the portion of the collection of resin particles in which the resin particles all have the same composition as each other is, by weight based on the dry weight of the entire collection of resin particles, 50% or more; more preferably 75% or more; more preferably 90% or more; more preferably 95% or more.

Preferably the resin particles comprise polymerized units of one or more monovinyl monomer and polymerized units of one or more multivinyl monomer. Preferred monovinyl monomers are monovinyl vinyl aromatic monomers, monovinyl acrylic monomers, and mixtures thereof; more preferred are monovinyl aromatic monomers; more preferred is styrene. Preferred multivinyl monomers are divinylbenzene, allyl (meth)acrylate, monomers having two or more (meth)acrylate groups, and mixtures thereof; more preferred is divinylbenzene.

The resin particles of the present invention contain covalently bound acid functional groups. Preferred acid functional groups are carboxyl groups, phosphorous acid groups, sulfonic acid groups, and mixtures thereof. Preferred are sulfonic acid groups. Phosphorous acid groups are groups that contain phosphorous, oxygen, and hydrogen and that contain at least one OH group bound to the phosphorous atom. The acid functional groups may be in hydrogen form or in salt form with one or more cationic counterion or a combination thereof.

The acid functional groups may be introduced by any method. For example (method I), the acid functional group may be covalently bound to a monomer prior to the polymerization process that forms the resin, with the polymerization process conducted in a way that preserves the acid functional group. Preferably (method II), acid functional groups are attached to the resin by chemical reaction after the polymerization process that formed the resin is complete. For example, a resin containing polymerized units of one or more vinyl aromatic monomer could be made; and the resin could then be contacted with sulfuric acid to attach sulfonic acid groups to the resin via a covalent bond between the sulfur atom of the sulfonic acid group and a carbon atom present in an aromatic ring.

To characterize the amounts of polymerized units of particular monomers that are present in a resin, the following procedure is used. It is imagined that all of the acid functional groups are replaced by hydrogen atoms to form an imaginary polymer, and the weight % of polymerized units of a particular monomer is determined for the imaginary polymer, and that weight % is used to characterize the actual finished polymer. This procedure is easy to envision for resins made by method II defined above. The polymerization is conducted to form a copolymer, and the weight % of each type of monomer, based on the weight of that copolymer, is characterized. After the chemical reaction is conducted to introduce acid functional groups, the finished resin, bearing acid functional groups, is still described by the weight % figures that were determined for the copolymer prior to the introduction of the acid functional groups. For example, a copolymer could be made using 97% by weight styrene and 3% by weight divinylbenzene, based on the total weight of monomers. The resulting copolymer would have 97% by weight polymerized units of styrene and 3% by weight polymerized units of divinylbenzene. After the copolymer was subjected to contact with sulfuric acid to introduce sulfonic acid groups, the resulting resin would still be described as having 3% polymerized units of divinylbenzene.

Preferably, the amount of polymerized units of multivinyl monomer in the resin is, by weight based on the dry weight of the resin, 0.5% or more; more preferably 1% or more; more preferably 2% or more; more preferably 3% or more. Preferably, the amount of polymerized units of multivinyl monomer in the resin is, by weight based on the dry weight of the resin, 7.9% or less; more preferably 7% or less; more preferably, 6% or less.

Preferably, the sum of the weight % of polymerized units of multivinyl monomer plus the weight % of polymerized units of monovinyl monomer, based on the dry weight of the resin, is 80% or more; more preferably 90% or more; more preferably 95% or more; more preferably 98% or more.

Preferably, the amount of polymerized units of vinyl aromatic monomer in the resin is, by weight based on the weight of the resin, 25% or more; more preferably 50% or more; more preferably 75% or more; more preferably 90% or more; more preferably 95% or more; more preferably 99% or more.

Preferably, the mole % of the acid functional groups covalently bound to the resin particles that are in hydrogen form is 50% or higher; more preferably 60% or higher; more preferably 70% or higher; more preferably 80% or higher; more preferably 90% or higher.

Preferably, the resin particles have total capacity of 0.5 eq/L or higher; more preferably 1 eq/L or higher. Preferably, the resin particles have total capacity of 5 eq/L or lower; more preferably 4 eq/L or lower; more preferably 3 eq/L or lower.

Preferably, the resin particles are gel resin particles.

The resin is present as a collection of resin particles. Preferably the collection of resin particles has D50 of 500 μm or less; more preferably 400 μm or less; more preferably 350 μm or less. Preferably UC of the collection of particles is 1.5 or lower; more preferably 1.4 or lower; more preferably 1.3 or lower; more preferably 1.2 or lower.

The present invention involves the use of an aqueous solution. The aqueous solution comprises one or more sugars and additionally comprises one or more furfurals (i.e., furfural, hydroxymethylfurfural, or a mixture thereof). In the practice of the present invention, the aqueous solution is passed through a collection of resin particles. It is contemplated that the interaction between the resin particles and the one or more furfurals will be a stronger interaction than any interaction between the resin particles and any other compound in the aqueous solution. Therefore it is contemplated that all the compounds in the aqueous solution will pass through the collection of resin particles more quickly than the one or more furfurals will pass through the collection of resin particles. Thus the process of the present invention will serve to separate the one or more furfurals from the remainder of the compounds dissolved in the aqueous solution.

The aqueous solution contains one or more sugars. Preferably the aqueous solution contains glucose.

Preferably the aqueous solution contains one or more organic acid. Preferred acids have atoms of hydrogen, carbon, and oxygen only. Preferred acids have pKa or 1 or higher; more preferred acids have pKa of 1.4 or higher; more preferred acids have pKa of 1.8 or higher. Preferred acids have pKa of 6.5 or lower; more preferred acids have pKa of 6 or lower; more preferred acids have pKa or 5.5 or lower; more preferred acids have pKa of 5 or lower. Preferably, the aqueous solution contains one or more organic acids having exactly one carboxyl group per molecule. Preferably, the aqueous solution contains one or more organic acids having two or more carboxyl groups per molecule. Preferably, the aqueous solution contains a mixture of one or more organic acids having exactly one carboxyl group per molecule and one or more organic acids having two or more carboxyl groups per molecule. Preferably, the aqueous solution contains two or more organic acids; more preferably four or more organic acids.

Preferably the aqueous solution contains one or more alcohol. Preferred alcohols are organic compounds; more preferred alcohols have atoms of carbon, hydrogen, and oxygen only. Preferred alcohols have 10 or fewer carbon atoms per molecule; more preferred alcohols have 8 or fewer carbon atoms per molecule; more preferred alcohols have 6 or fewer carbon atoms per molecule; more preferred alcohols have 4 or fewer carbon atoms per molecule. Preferably, the aqueous solution contains one or more alcohol having exactly one hydroxyl group per molecule. Among alcohols having exactly one hydroxyl group per molecule, ethanol is preferred. Preferably, the aqueous solution contains one or more alcohol having two or more hydroxyl groups per molecule. Among alcohols having two or more hydroxyl groups per molecule, glycerol is preferred.

Preferably, the aqueous solution contains one or more inorganic salt. Preferably, every inorganic salt that is present in the aqueous solution is dissolved in the aqueous solution. Inorganic salts have the structure MA. M is a cationic moiety; preferred M cations are ammonium, alkali metals, alkaline earths, transition metals, and mixtures thereof; more preferred are ammonium, alkali metals, and mixtures thereof; more preferred are alkali metals and mixtures thereof; more preferred is sodium. A is an anionic moiety; preferred A anions are hydroxide, cyanide, thiocyanate, hypochlorite, chlorite, chlorate, perchlorate, nitrite, nitrate, permanganate, carbonate, chromate, dichromate, sulfite, sulfate, phosphite, phosphate, and mixtures thereof; more preferred are nitrite, nitrate, carbonate, sulfite, sulfate, phosphite, phosphate, and mixtures thereof; more preferred are nitrate, carbonate, sulfate, phosphate, and mixtures thereof.

Preferably, the pH of the aqueous solution is 6 or less; more preferably 5 or less; more preferably 4 or less; more preferably 3 or less; more preferably 2 or less.

The present invention involves passing the aqueous solution through a collection of resin particles. The collection of resin particles is preferably contained in a vessel. Preferably, the vessel prevents the collection of particles from escaping the vessel and also allows aqueous solution to enter the vessel, to pass through the collection of resin particles, and to exit the vessel.

Preferably, the process of the aqueous solution passing through the collection of resin particles involves contact between the aqueous solution and resin particles. Preferably, the collection of resin particles is contained in a vessel, and while the aqueous solution is passing through the collection of resin particles, 50% or more of the resin particles by volume, based on the volume of the collection of resin particles, are in contact only with other resin particles, the aqueous solution, the interior surface of the vessel, or a combination thereof.

Preferably, the vessel containing the collection of resin particles is a column. A column has an inlet for the aqueous solution and an outlet for the aqueous solution. Preferably, the outlet is located opposite to the inlet. The line from the inlet to the outlet determines the "length" dimension of the vessel. Preferably, the length of the interior of the vessel is greater than any dimension of the interior of the vessel that is perpendicular to the length. A planar slice of the interior of the vessel taken perpendicular to the length is a cross section. Preferably, the cross section is the same over 90% or more of the length of the vessel. Preferred cross section is circular. A preferred category of vessels are columns suitable for use in chromatography.

Preferably, the aqueous solution is forced into the inlet of the vessel, passes through the collection of resin particles, and passes out of the vessel through the outlet due to pressure. The pressure may be caused by gravity or by a mechanical device such as a pump.

Preferably, all of the compounds dissolved in the aqueous solution will be carried through the collection of resin particles and will exit the vessel through the outlet. It is contemplated that each dissolved compound will be somewhat retarded in its passage through the collection of resin particles due to interaction of the dissolved compound with the resin particles. Preferably, furfural (if present) and hydroxymethylfurfural (if present) will be more retarded than any of the other dissolved compounds in the aqueous solution.

Two preferred embodiments are "pulse embodiments" and "SMB embodiments."

In pulse embodiments, a preliminary aqueous solution is provided. The preliminary aqueous solution preferably has all the required and preferred characteristics of the aqueous solution of the present invention as described above. In pulse embodiments, a fixed amount of preliminary aqueous solution is added to the vessel through the inlet of the vessel. Preferably, the amount of preliminary aqueous solution is 0.01 BV or more; more preferably 0.02 BV or more; more preferably 0.03 BV or more; more preferably 0.04 BV or more. Preferably, the amount of preliminary aqueous solution is 0.5 BV or less; more preferably 0.2 BV or less; more preferably 0.1 BV or less. Then, a fluid known as the eluent is added continuously to the vessel through the inlet, causing fluid to pass through the collection of resin particles and to exit the vessel through the outlet. The fluid exiting the vessel is collected and analyzed. Preferably, there will be a time period during which the fluid exiting the vessel contains one or more compounds that were present in the preliminary aqueous solution and either contains no amount of one or more furfurals or else contains a negligible amount of one or more furfurals. Preferably, at some later time the fluid exiting the vessel contains one or more furfurals and either contains no amount of any other compound that was dissolved in the preliminary aqueous composition or else contains a negligible amount of any other compound that was dissolved in the preliminary aqueous solution.

The term "negligible amount" is determined as follows. Two compounds C1 and C2 that are present in the preliminary aqueous solution have an initial weight quotient of $$Q0=(WC10)/(WC20)$$

where WC10=(concentration of C1 in grams per liter in the preliminary aqueous solution), and WC20=(concentration of C2 in grams per liter in the preliminary aqueous solution). The fluid exiting the vessel at some specific time T will have a weight quotient $$QT=(WC1T)/(WC2T)$$

where WC1T=(concentration of C1 in grams per liter in the exiting aqueous solution at time T), and WC2T=(concentration of C2 in grams per liter in the exiting aqueous solution at time T). Then, if the fluid exiting the vessel at time T contains C1, the amount of C2 is considered negligible at time T if QT is equal to or greater than $100*Q0$.

Preferably, in a pulse embodiment, the eluent is an aqueous solution having pH of 5 or lower; more preferably 4 or lower; more preferably 3 or lower; more preferably 2 or lower. Preferably, the eluent is a solution of one or more inorganic acids in water. Preferably, the eluent contains 0 to 0.01% of any compound other than inorganic acid and water. Preferred inorganic acids for use in the eluent are hydrochloric acid, sulfuric acid, and mixtures thereof; more preferred is sulfuric acid. Preferably, the eluent is a solution of one or more inorganic acids in water. When the eluent is a solution of one or more inorganic acids in water, preferably the total concentration of inorganic acid is 10 g/L or less; more preferably 5 g/L or less; more preferably 3 g/L or less. When the eluent is a solution of one or more inorganic acids in water, preferably the total concentration of inorganic acid is 0.2 g/L or more; more preferably 0.5 g/L or more; more preferably 1 g/L or more.

In pulse embodiments, the preferred flow rate is 1 BV per hour or higher; more preferably 1.5 BV per hour or higher; more preferably 2 BV per hour or higher; more preferably 2.5 BV per hour or higher. In pulse embodiments, the preferred flow rate is 10 BV per hour or less; more preferably 8 BV per hour or less; more preferably 6 BV per hour or less; more preferably 4 BV per hour or lower.

Preferred are SMB embodiments, which involve the use of a simulated moving bed (SMB). SMB methods are known, as explained for example by M. Juza, et. al, in "Simulated moving-bed chromatography and its application to chirotechnology," *Trends in Biotechnology*, volume 18, pages 108-118, March 2000. In a simulated moving bed method, a plurality of identical columns is arrayed in a continuous loop. Eluent passes under pressure through the loop in one direction, the "downstream" direction. Valves and pipes are arranged so that inlet and outlet points are periodically moved from one point in the loop to the next in the downstream direction, at a rate in between the rates R1 and R2, where R1 is the rate of progress through the column of slower-eluting species, and R2 is the rate of progress through the column of faster-eluting species. The inlet apparatus uses pipes and valves to introduce preliminary aqueous solution into the loop. An outlet apparatus is located upstream of the inlet apparatus; this outlet apparatus uses pipes and valves to remove eluent that is relatively rich in slower-eluting dissolved species from the loop. A second outlet apparatus is located downstream of the inlet apparatus; this outlet apparatus uses pipes and valves to remove eluent that is relatively rich in faster-eluting dissolved species from the loop.

For SMB embodiments, the required and preferred features of the preliminary aqueous solution are the same as described above for the preliminary aqueous solution used in pulse embodiments. For SMB embodiments, the required and preferred features of the eluent are the same as described above for the eluent used in pulse embodiments. For SMB embodiments, the preferred flow rate is the same as for pulse embodiments as described above.

Preferably, the method of the present invention is conducted at a temperature of 20° C. or higher; more preferably 25° C. or higher; more preferably 30° C. or higher; more preferably 35° C. or higher; more preferably 40° C. or higher. Preferably, the method of the present invention is conducted at a temperature of 80° C. or lower; more preferably 70° C. or lower; more preferably 60° C. or lower.

The following are examples of the present invention.

EXAMPLE 1: PULSE TEST

A preliminary aqueous solution was prepared by dissolving exactly one of the compounds below in a solvent made by dissolving 2 grams of sulfuric acid per liter of water. Each solute was present at 20% by weight or else by the maximum solubility in the solvent, whichever was lower.

The resin was a gel resin having polymerized units of styrene and divinylbenzene and having sulfonic acid groups. The amount of polymerized units of divinylbenzene, by weight based on the weight of the resin, was between 3 and 6%. D50 was 310 μm, and UC was 1.2. Total capacity was between 1.3 and 1.75.

A packed bed of resin particles (91 cm long by 2.7 cm diameter) was prepared in a chromatography column. The amount of preliminary aqueous solution loaded onto the top of the column was 0.05 BV (26.1 mL). The eluent was a solution of 2 g/L of sulfuric acid in water. Eluent flowed through the column at 3.0 BV per hour. The process was conducted at 53° C. Elution fractions were collected at the exit of 8 mL each (0.015 BV)

Each fraction was analyzed using a Reichert™ AR200 refractometer. Compound standards of known concentration were used to convert refractometer signal into concentration in g/L. For each compound, this procedure generated a curve of concentration versus BV.

The entire procedure was repeated for each of the compounds listed below.

The mean ($\mu_1$) and variance ($\mu_2$) for each such curve is reported below. Mean and variance were calculated as follows. Retention "times" were measured in BV. Equation 1 below was used to calculate the retention time ($t_i$) of a given fraction i:

$$t_i = t_{delay} + t_{elution,i} + t_{deadvolume} \quad \text{(Eq. 1)}$$

Where $t_{delay}$ is the delay before starting the fraction collector, $t_{elution,i}$ is the time after starting is the fraction collector where the midpoint of a given fraction i comes out, and $t_{deadvolume}$ is added delay caused by system dead volume as discussed above. $t_{delay}$ was measured directly by the pulse test operator, while $t_{elution,i}$ and $t_{deadvolume}$ were calculated using Equations 2 and 3 respectively below:

$$t_{elution,i} = (i - 0.5) * t_{fraction} \quad \text{(Eq. 2)}$$

$$t_{deadvolume} = \frac{1}{F} * \left(V_{piping} + \frac{V_{Loop}}{2}\right) \quad \text{(Eq. 3)}$$

Where in Eq. 2 i is the fraction number and $t_{fraction}$ is the collection time of each fraction programmed into the fraction collection. In Eq. 3 F is the system flow rate, $V_{piping}$ is the estimated volume of piping (outside of the column itself) that the sugar pulse must travel to get from the sample loop to the fraction collector, and $V_{Loop}$ is the sample loop volume. The sample loop is a small piece of tubing which holds the preliminary aqueous solution prior to loading on the column.

$C_{x,i}$ is the normalized concentration of a component x (e.g. glucose, fructose, or maltose) in fraction i. The concentrations of each component were then normalized to the pulse feed concentration. Thus, the calculation for $C_{x,i}$—the normalized concentration of component x in a pulse test fraction—is:

$$C_{x,i} = \frac{A_{x,i}}{A_{x,Pulse}} \quad \text{(Eq. 4)}$$

where $A_{x,i}$ is the peak area (undiluted) of component x in fraction i, and $A_{x,Pulse}$ is the peak area (undiluted) of component x in the pulse feed.

With $t_i$ and $C_{x,i}$ determined, the first peak moment, $\mu_1$, (the arithmetic mean of the peak), was calculated for each component x using Eq. 5 below:

$$\mu_{1,x} = \frac{\sum_n [C_{x,i} * t_i * t_{fraction}]}{\sum_n [C_{x,i} * t_{fraction}]} \quad \text{(Eq. 5)}$$

where $t_{fraction}$ on is again the time between fractions and n is the total number of fractions analyzed.

The value of $\mu_2$ for component x, the peak variance, is calculated using Eq. 6 below:

$$\mu_{2,x} = \frac{\sum_n [C_{x,i} * t_i^2 * t_{fraction}]}{\sum_n [C_{x,i} * t_{fraction}]} - \mu_{1,x}^2 \quad \text{(Eq. 6)}$$

In the results below, standard deviation (sd) is reported, where sd is the square root of $\mu_2$.

Results were as follows, in units of BV:

| compound | mean | sd |
|---|---|---|
| Furfural | 1.677 | 0.281 |
| Hydroxymethylfurfural | 1.724 | 0.106 |
| Acetic Acid | 0.705 | 0.079 |
| Ascorbic Acid | 0.573 | 0.098 |
| Citric Acid | 0.544 | 0.109 |
| Gluconic Acid | 0.663 | 0.133 |
| Maleic Acid | 0.604 | 0.108 |
| Malic Acid | 0.645 | 0.141 |
| Propionic Acid | 0.771 | 0.117 |
| Sodium Sulfate | 0.472 | 0.052 |
| Succinic Acid | 0.668 | 0.102 |
| Glucose | 0.522 | 0.085 |
| Glycerol | 0.715 | 0.088 |
| Glycolic Acid | 0.746 | 0.09 |
| Itaconic Acid | 0.698 | 0.12 |
| Lactic Acid | 0.77 | 0.128 |
| Levulinic Acid | 0.754 | 0.156 |
| Tartaric Acid | 0.61 | 0.103 |
| 2-Ketoglutaric Acid | 0.572 | 0.107 |
| Ethanol | 0.794 | 0.097 |
| Saccharic Acid | 0.539 | 0.125 |

The furfural and the hydroxymethylfurfural both elute much later that all the other compounds, as shown by the mean values of elution time. Also, the furfural and hydroxymethylfurfural peaks do not significantly overlap with any of the peaks from the other compounds, as shown by the standard deviation (sd) values. This result demonstrates that the furfurals could readily be separated from any mixture of the other compounds using the method employed.

It is contemplated that the pulse test is an accurate predictor of the efficacy of an SMB method. That is, it is expected that an SMB method conducted using materials similar to Example 1 would yield results similar to those of Example 1.

COMPARATIVE EXAMPLE 2C

Pulse tests using the procedure in Example 1 were conducted. The resin was a crosslinked acrylic gel resin with tertiary amine functional groups, total capacity of 1.6 eq/L or greater, harmonic mean particle size of 400 to 500 µm, and uniformity coefficient of 1.3 or less. Each of the following compounds showed an elution curve (i.e., a curve of concentration in the exit fraction versus time) that overlapped substantially with the elution curve of either furfural or hydroxymethylfurfural or both: sodium sulfate, acetic acid, lactic acid, gluconic acid, glucose, glycerol, ethanol, levulinic acid, and propionic acid. The procedure was not useful for separating furfurals from aqueous solutions containing any of these compounds.

COMPARATIVE EXAMPLE 3C

Pulse tests using the procedure in Example 1 were conducted. The resin had quaternary ammonium functional groups, volume-average particle diameter of 300 μm, and uniformity coefficient of less than 1.2.

Each of the following compounds showed an elution curve (i.e., a curve of concentration in the exit fraction versus time) that overlapped substantially with the elution curve of either furfural or hydroxymethylfurfural or both: citric acid, tartaric acid, propionic acid, succinic acid, acetic acid, and lactic acid. The procedure was not useful for separating furfurals from aqueous solutions containing any of these compounds.

COMPARATIVE EXAMPLE 4C

Pulse tests using the procedure in Example 1 were conducted. The resin was an adsorbent resin with no acid functional groups and no amine functional groups. Furfural and hydroxymethylfurfural bound to the resin and did not elute with the eluent described above. Consequently it was judged that the adsorbent resin is unsuitable for the present method, because, even if separation between the furfurals and other compounds were to be achieved, the resin would have to periodically be subjected to a regeneration process to remove the furfurals, and such regeneration processes are undesirable.

The invention claimed is:

1. A process for purifying an aqueous solution, wherein the aqueous solution comprises one or more sugars, two or more organic carboxylic acids and additionally comprises furfural, hydroxymethylfurfural, or a mixture thereof, wherein the process comprises passing the aqueous solution through a bed of resin particles at a temperature from 40° C. to 80° C., followed by passing an aqueous solution containing one or more inorganic acids through said bed to elute the one or more sugars, two or more organic carboxylic acids, furfural, and hydroxymethylfurfural from the bed, wherein the furfural and hydroxymethyfurfural elute from the bed much later than the one or more sugars and two or more organic carboxylic acids thereby separating furfural and hydroxymethylfurfural from said one or more sugars and said two or more organic carboxylic acids without binding furfural and hydroxymethylfurfural to the resin particles, wherein the resin particles comprise 90 wt % or more polymerized units of vinyl aromatic monomer and comprise covalently bound sulfonic acid functional groups and wherein 50 mole % or more of the acid functional groups covalently bound to the resin particles are in hydrogen form.

2. The process of claim 1, wherein the resin particles have volume-average diameter of 400 μm or less.

3. The process of claim 1, wherein the resin particles have uniformity coefficient of 1.2 or less.

4. The process of claim 1, wherein the aqueous solution comprises four or more organic carboxylic acids and additionally comprises one or more inorganic salts, one or more alcohols, or a mixture thereof.

* * * * *